(12) United States Patent
Yokoyama et al.

(10) Patent No.: US 6,937,694 B2
(45) Date of Patent: Aug. 30, 2005

(54) POLE MEASURING METHOD

(75) Inventors: Ryouichi Yokoyama, Akishima (JP); Kazuhiko Omote, Akishima (JP); Kamihisa Endo, Akishima (JP); Ryuji Matsuo, Akishima (JP)

(73) Assignee: Rigaku Corporation, Tokyo (JP)

( * ) Notice: Subject to any disclaimer, the term of this patent is extended or adjusted under 35 U.S.C. 154(b) by 342 days.

(21) Appl. No.: 10/129,415

(22) Filed: May 1, 2002

(65) Prior Publication Data

US 2003/0012335 A1 Jan. 16, 2003

Related U.S. Application Data

(63) Continuation-in-part of application No. 09/591,273, filed on Jun. 9, 2000, now abandoned.

(30) Foreign Application Priority Data

Jun. 10, 1999 (JP) .......................................... 11-164490

(51) Int. Cl.[7] ........................................... G01N 23/207

(52) U.S. Cl. ............................. 378/78; 378/70; 378/71; 378/73; 378/86

(58) Field of Search .............................. 378/70, 71, 72, 378/73, 74, 75, 78, 81, 82

(56) References Cited

FOREIGN PATENT DOCUMENTS

JP          2001-56304          2/2001

OTHER PUBLICATIONS

Nov. 11, 1998 Grazing Incidence In–Plane Diffractometer for Thin–Films Kazuhiko Omote et al. X–sen Bunseki no Shinpo vol. 30 pp. 205–218.

1999 Dai 50 kai Sosei Kako Rengo Kouenkai Kouen Ronbunshuu, (Japan) pp. 35–36.

*Primary Examiner*—Edward J. Glick
*Assistant Examiner*—Courtney Thomas
(74) *Attorney, Agent, or Firm*—Jordan and Hamburg LLP

(57) ABSTRACT

A method for measuring a pole of a sample, using a reflection method, is effective substantially over all measurement regions ranging from the region of high-tilting-angle $\alpha$ of a conventional pole measuring to the in-plane diffraction region corresponding to low-tilting-angle $\alpha$.

3 Claims, 8 Drawing Sheets

POLE MEASURING METHOD

REFERENCE TO RELATED APPLICATION

This is a continuation-in-part of U.S. patent application Ser. No. 09/591,273, filed Jun. 9, 2000 now abandoned.

TECHNICAL FIELD

The present invention relates to a pole measuring method for analyzing polycrystalline samples by using an X-ray diffractometer.

BACKGROUND ART

As one of pole measuring methods for analyzing a polycrystalline sample using an X-ray diffractometer, there is a pole measuring method for analyzing preferred orientation (texture) and the like of the sample by using a pole figure. The pole figure refers to a figure representing poles with respect to a specified lattice plane of crystallites constituting the sample by a polar net (a stereographic projection) as shown in FIG. 6. Here, the term "pole" signifies an intersection of the normal to a lattice plane with a projection sphere about the crystallites constituting the sample.

FIG. 5 is a schematic view explaining a conventional pole measuring method using a four-axis X-ray diffractometer.

As shown in FIG. 5, the sample S is rotated in directions of $\omega$ about an axis $\Omega$, and is rotatable about an axis $\psi$ in the surface Sa of the sample S. Also, the sample S is in-plane rotated about an axis $\Phi$ perpendicular to the sample surface Sa. These axes $\Omega$, $\psi$, and $\Phi$ intersect one another at the origin on the sample surface Sa (generally at the center of the sample). An incident X-ray $X_0$ is applied to the sample surface Sa at an incident angle $\theta$ along an equator plane. The setting of the incident angle $\theta$ is performed by the $\omega$-rotation of the sample S. Here, the equator plane shown in FIG. 5 refers to a horizontal plane passing the origin O and perpendicular to the $\Omega$-axis.

An X-ray detector 1 is mounted on a counter arm which rotates about the $\Omega$-axis along the equator plane. In the pole measuring, the X-ray detector 1 is generally disposed at the symmetrical position on the equator plane which satisfies a Bragg's diffraction condition, that is, a position in the direction of a diffracting angle of an X-ray equal to the incident angle $\theta$ of the X-ray with respect to the sample surface Sa. Specifically, the X-ray detector 1 is positioned, by revolving the counter arm about the $\Omega$-axis, at an angle of $2\theta$ with respect to the incident X-ray $X_0$ which is applied to the sample at the incident angle $\theta$.

The sample S is rotated about the $\psi$-axis in minute angle units (tilting angle $\alpha$), and is in-plane rotated about the $\Phi$-axis at each predetermined angle. In this manner, with each of the tilting angles $\alpha$ and each of the in-plane rotation angles $\beta$ as parameters, a diffracted X-ray $X_1$ which is a Bragg diffraction by the sample surface Sa is measured by the X-ray detector 1, disposed on the equator plane and fixed at a position at an angle of $2\theta$ with respect to the direction of the incident X-ray $X_0$.

By representing these measurement results on a graph named as a polar net, a pole figure is produced. In the polar net, the tilting angles $\alpha$ are shown in radial directions thereof, and the tilting angle $\alpha$ is defined so that $\alpha=90°$ at the center thereof, and that $\alpha=0°$ at the outer periphery thereof. When the sample surface Sa is perpendicular to the equator plane, the tilting angle $\alpha$ is 90°. In the polar net, the in-plane rotation angle $\beta$ is shown in the circumferential direction thereof.

FIG. 7 shows an example of pole figure with a pole of (111) of cold-rolled CuZn in which the ratio of Cu to Zn is 70 to 30.

In the conventional pole measuring, an X-ray beam of line-shaped cross-section is used as an incident X-ray, and therefore, when the tilting angle becomes small, that is, when the sample surface is tilted to a position near the horizontal plane in FIG. 5, the irradiation width of the incident X-ray with respect to the sample surface enlarges, and only one portion of the incident X-ray contributes to diffraction, thereby significantly reducing the intensity of the incident X-ray. As a result, in a low region of the tilting angle $\alpha$, a reflection method, in which a diffracted X-ray is reflected from the sample surface outwardly, does not allow the poles to be measured.

Accordingly, in a low angle region, a transmission method, in which a diffracted X-ray transmitted through the sample is measured, has been hitherto used for a pole measuring. In general, the reflection method has been used when the tilting angle $\alpha$ is in a range of 90° to 25°, while the transmission method has been used when the tilting angle $\alpha$ is in a range of 25° to 0°.

However, in the measurement by transmission, the intensity of a transmitted X-ray is reduced by the self-absorption. This has raised a problem that, since a sufficient intensity of X-ray cannot be obtained with respect to thick samples or samples formed on a substrate, extremely thin samples alone have been measurable. Hitherto, therefore, the pole measuring with respect to these thick samples and thin-film samples formed on a substrate have not been possible in a low region of the tilting angle $\alpha$.

DISCLOSURE OF INVENTION

Accordingly, it is an object of the present invention to realize a pole measuring, using the reflection method, substantially over all measurement regions ranging from the region of high-tilting-angle $\alpha$ in the conventional pole measuring to the in-plane diffraction region corresponding to low-tilting-angle $\alpha$.

Here, the in-plane diffraction refers to a diffraction phenomenon wherein, as shown in FIG. 8, when an X-ray $X_0$ is applied to the sample surface Sa at a small incident angle $\delta$, a component of the X-ray extending parallel to the sample surface Sa occurs within the sample S, the X-ray component is diffracted by a crystal plane P perpendicular to the sample surface Sa, and a diffracted X-ray $X_2$ goes out of the sample surface Sa at a very small angle with respect to the sample surface Sa.

The pole measuring method according to the present invention is implemented by using an X-ray diffractometer named as an in-plane diffractometer and having the following functions. That is, as shown in FIG. 1, the in-plane diffractometer is operable for rotating the sample S in a direction of $\omega$ about the $\Omega$-axis passing through the origin on the sample surface Sa (generally the center of the sample), revolving the X-ray detector 1 by an angle of $2\theta$ about the $\Omega$-axis along a first plane P1 (the equator plane) perpendicular to the $\Omega$-axis, and also revolving the X-ray detector 1 by an angle of $2\theta_\chi$ about the origin O along a second plane P2 including the $\Omega$-axis and perpendicular to the first plane P1.

The sample S is arranged so that the surface Sa thereof is disposed on the $\Omega$-axis, and that an incident X-ray $X_0$ is applied to the origin on the surface Sa thereof. The incident angle $\omega$ of the incident X-ray $X_0$ with respect to the sample surface Sa is set by the $\omega$-rotation of the sample S. The in-plane diffractometer has also a function of in-plane rotating (β-rotating) the sample S about the Φ-axis passing through the origin O and perpendicular to the sample surface Sa.

While the conventional four-axis X-ray diffractometer, as shown in FIG. 5, has been configured so as to detect a diffracted X-ray occurring on the equator plane (the plane passing through the origin O and perpendicular to the Ω-axis), the above-described in-plane diffractometer (see FIG. 1) allows a diffracted X-ray emitted onto a diffraction plane different from the equator plane (the plane passing through the origin O and perpendicular to the Ω-axis), to be detectable by setting 2θ- and $2\theta_\chi$-revolutions of the X-ray detector 1. Here, the diffraction plane refers to a plane on which an incident X-ray and a diffracted X-ray from the sample exist.

The present invention is characterized in that, by utilizing such characteristics of the in-plane diffractometer, a diffracted X-ray which is to occur on the equator plane when the sample S is tilted by the tilting angle α in the conventional pole measuring method using the four-axis X-ray diffractometer, is detected on a diffraction plane different from the equator plane, by the 2θ- and $2\theta_\chi$-revolutions of the X-ray detector 1, without need to tilt the sample.

That is, in the present invention, pole measuring is performed by a method including the following operations (a) to (d).

(a) On the basis of a preset tilting angle (α) of a sample, an incident angle (ω) of an X-ray with respect to the surface of the sample is set to a predetermined position corresponding to the pole measuring position when the sample is tilted by the tilting angle (α), by rotating the sample about a predetermined axis (Ω axis) passing through a predetermined origin (O).

(b) On the basis of the tilting angle (α), the X-ray detector is revolved by an angle (2θ) about the predetermined axis (Ω axis) along a first plane perpendicular to the predetermined axis (Ω axis) and also revolved by an angle ($2\theta_\chi$) about the origin (O) along a second plane including the predetermined axis (Ω axis) and perpendicular to the first plane, whereby the X-ray detector is disposed at a predetermined position corresponding to the pole measuring position when the sample is tilted by the tilting angle (α).

(c) On the basis of the tilting angle (α), a correction angle (Δβ) with respect to the measuring angle of the sample in an in-plane rotational direction is calculated, and a measuring angle (φ) of the sample in the in-plane rotational direction is set, the measuring angle (φ) being obtained by adding the correction angle (Δβ) to a preset measuring angle (β) of the sample in the in-plane rotational direction.

(d) Next, by detecting the diffracted X-rays diffracted from the sample surface Sa using the X-ray detector, a pole of the sample is obtained.

By this method, it is possible to achieve pole measuring by the reflection method over all measurement regions ranging from the region of high-tilting-angle α to the in-plane diffraction region, and to obtain highly accurate pole measuring data even with respect to thin-film samples and thick samples.

BEST MODE FOR CARRYING OUT THE INVENTION

Hereinafter, the preferred embodiment according to the present invention will be described with reference to the drawings.

Figure 1:
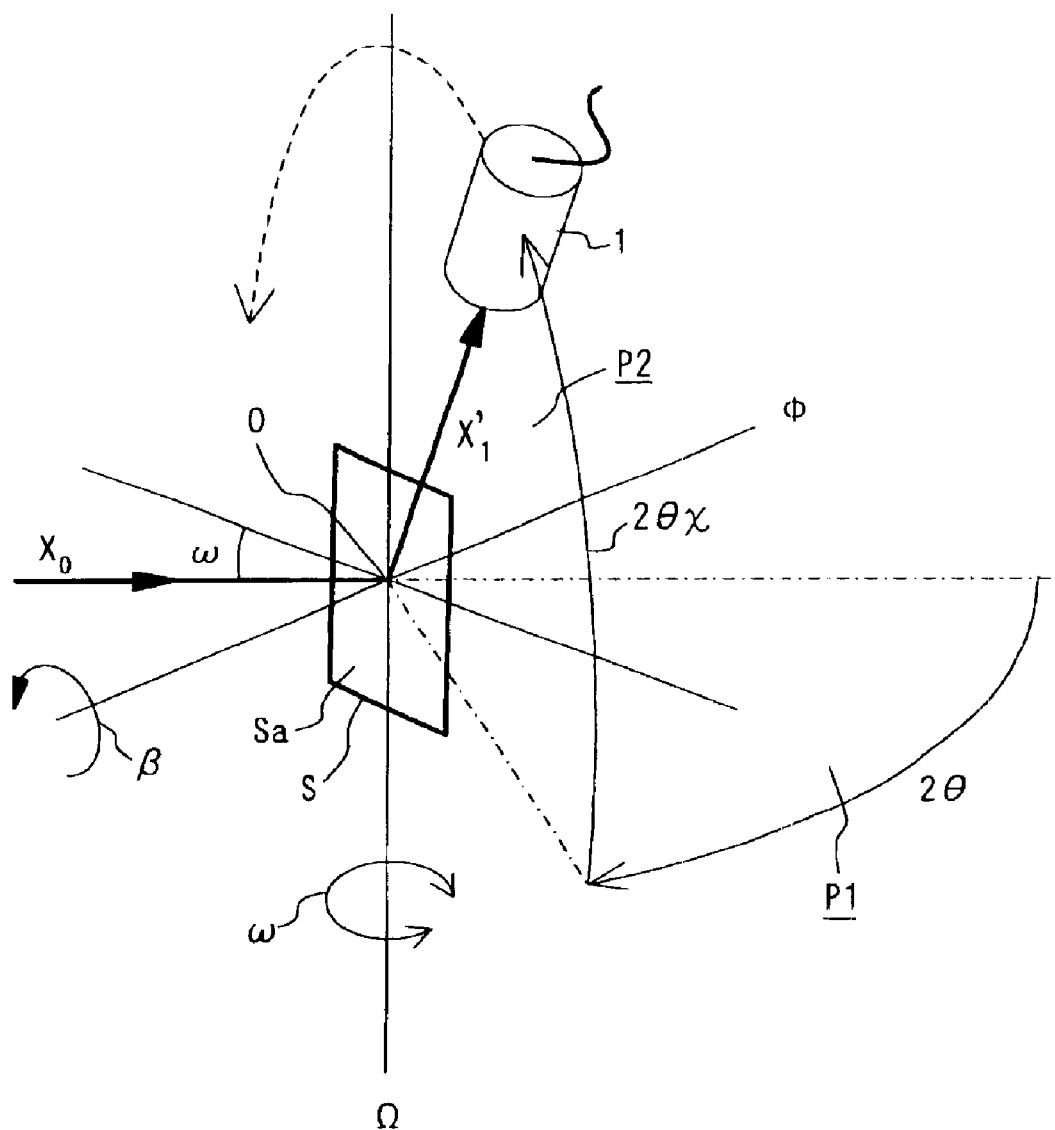
FIG. 1 is a schematic view showing an outline of an in-plane diffractometer used for the pole measuring method according to the present invention.
Figure 5:
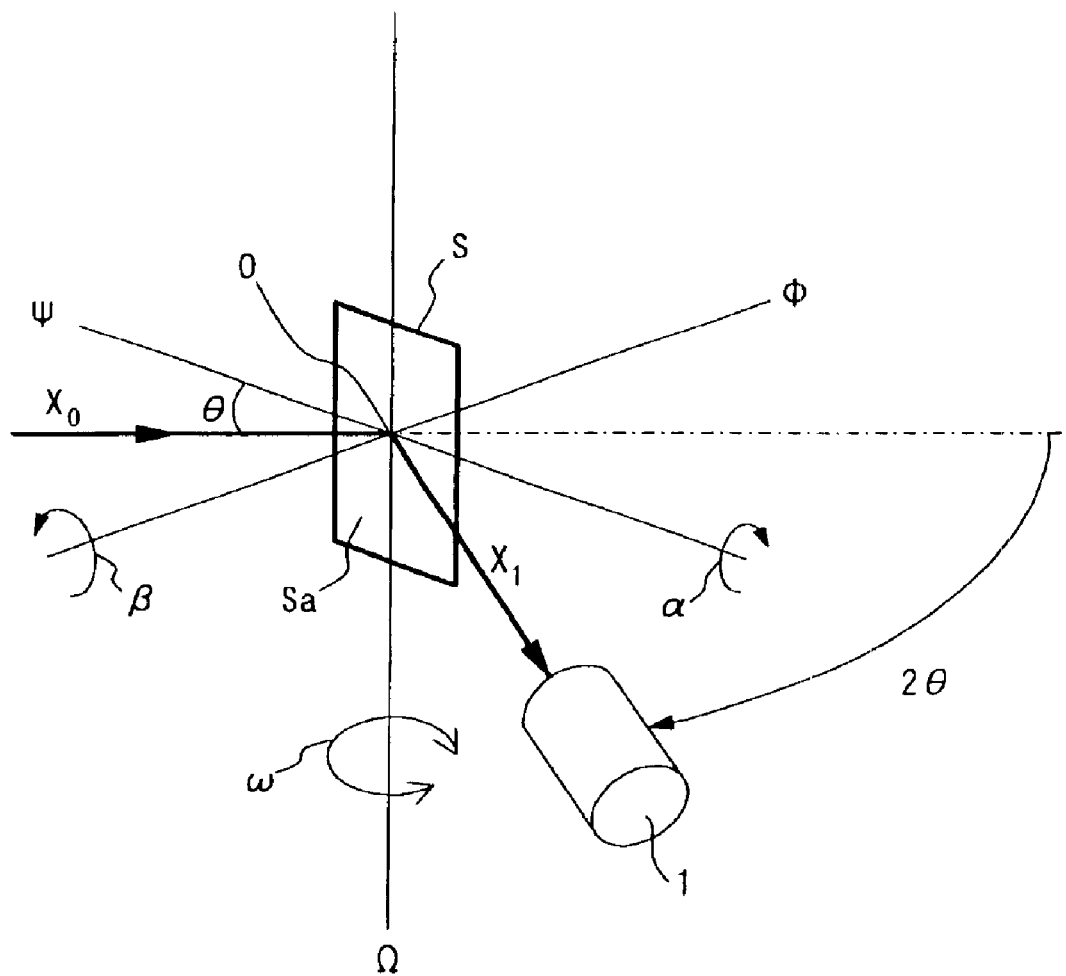
FIG. 5 is a schematic view explaining the principle of a conventional pole measuring method.
Figure 6:
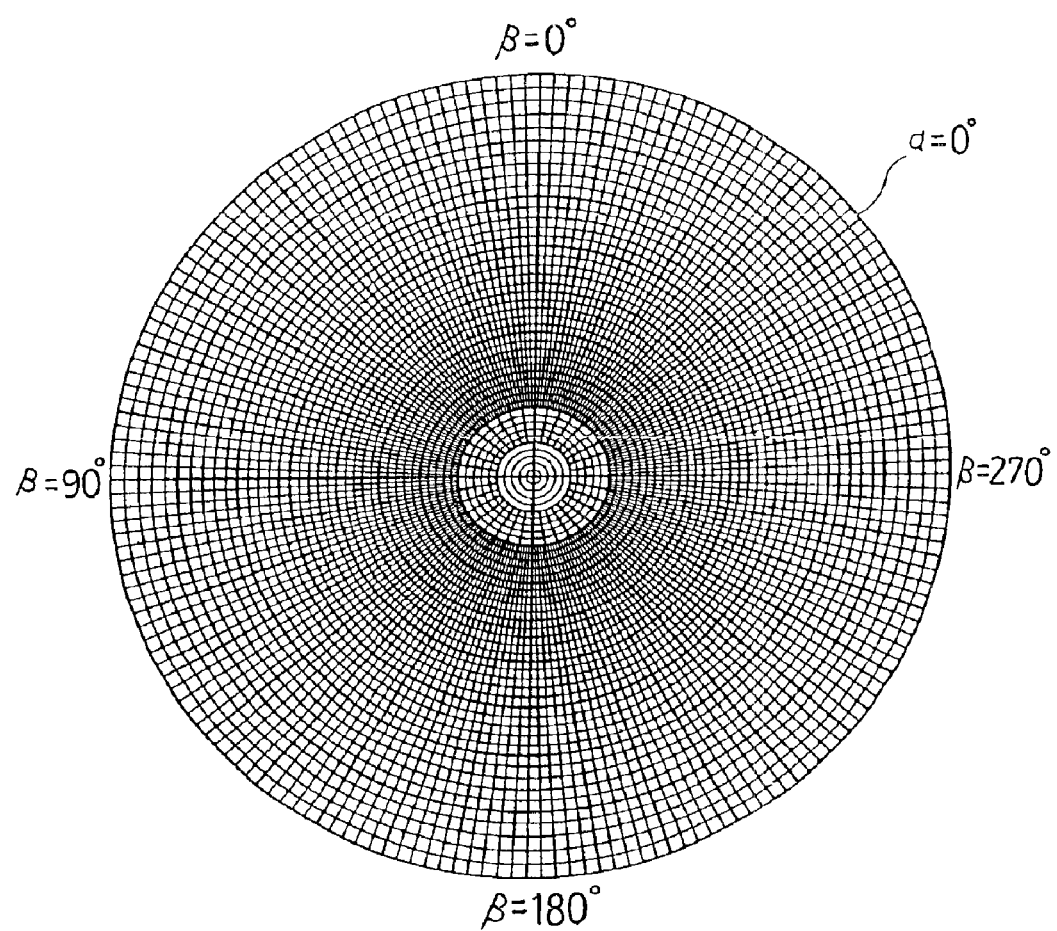
FIG. 6 is a view explaining a typical polar net.
Figure 7:
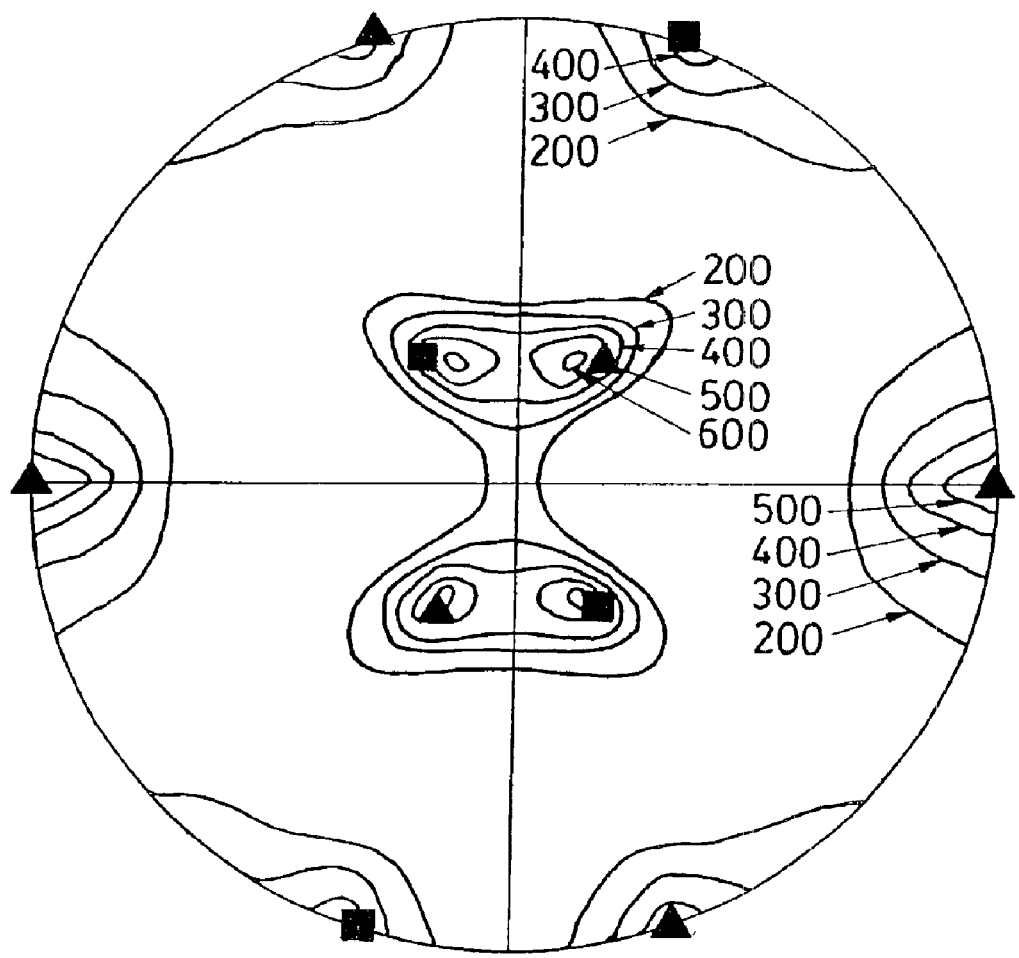
FIG. 7 is an illustration of a pole figure of poles with respect to (111) of cold-rolled CuZn in which the ratio of Cu to Zn is 70 to 30.
Figure 8:
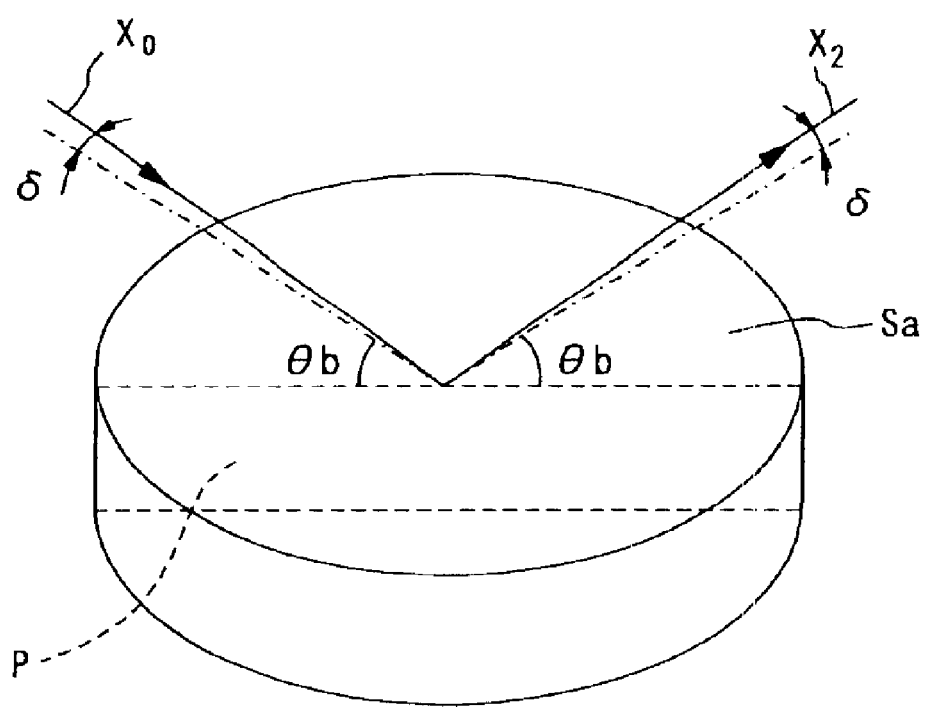
FIG. 8 is a perspective view explaining an in-plane diffraction.

In the pole measuring method according to this embodiment, by utilizing the in-plane diffractometer shown in FIG. 1, the X-ray detector is revolved by an angle of $2\theta_\chi$ instead of the tilting operation with respect to the sample surface Sa. By this revolution operation, a diffracted X-ray which is to occur on the equator plane at a tilting angle α when the conventional pole measuring method using the four-axis X-ray diffractometer (see FIG. 5) is practiced, is detected at a position of the X-ray diffractometer shifted by the $2\theta_\chi$-revolution.

Figure 2:
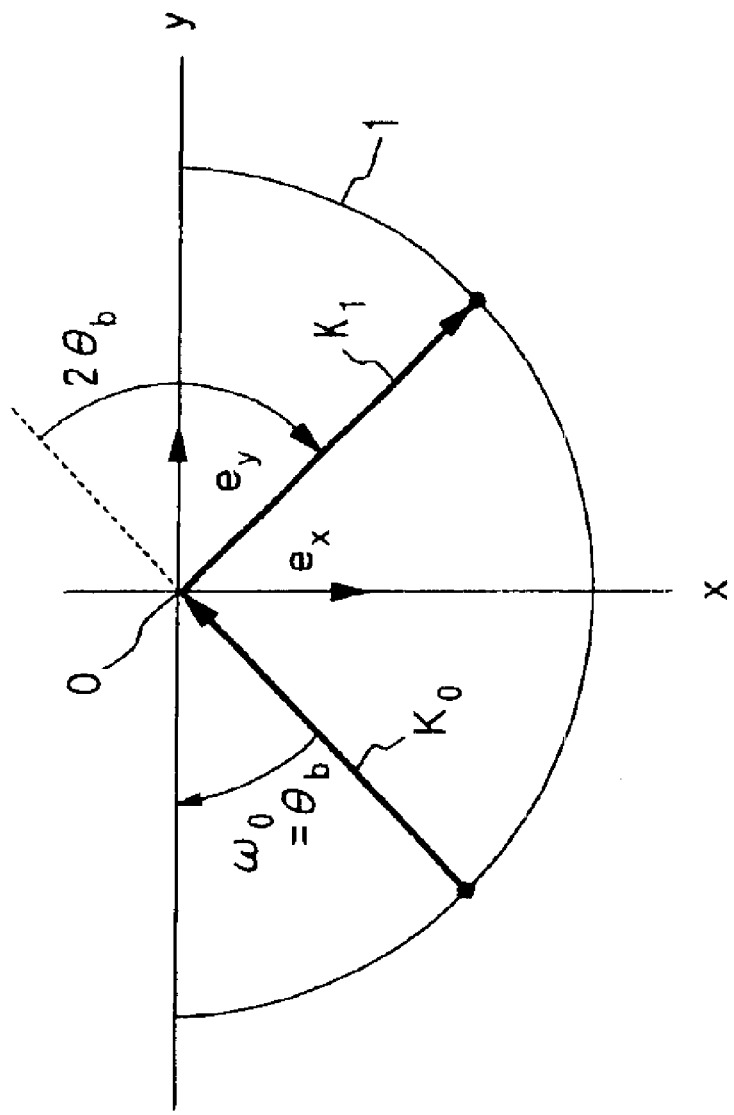
FIG. 2 is a plan view explaining the principle of the pole measuring method according to the present invention.
Figure 3A:
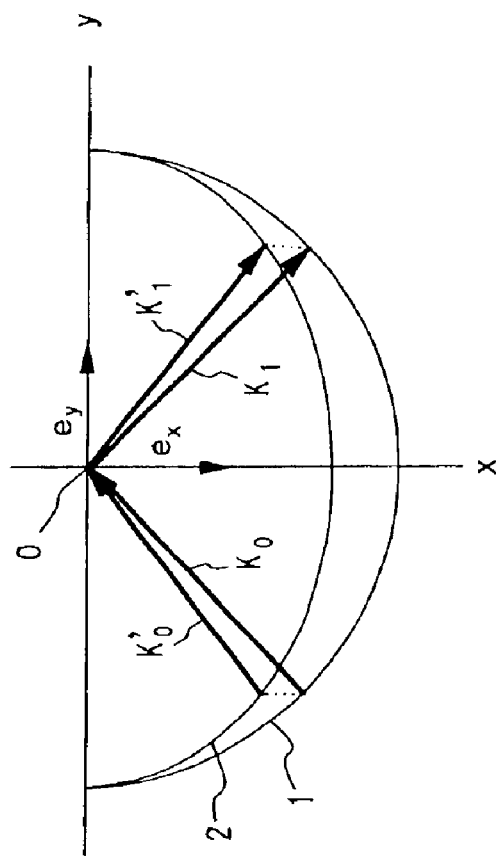
FIG. 3A is a plan view explaining the principle of the pole measuring method according to the present invention, as a follow-up view to FIG. 2.
Figure 3B:
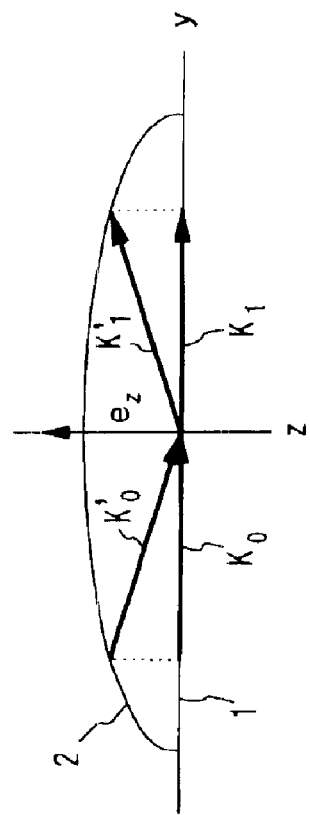
FIG. 3B is a front view explaining the principle of the pole measuring method according to the present invention, as a follow-up view to FIG. 2.
Figure 3C:
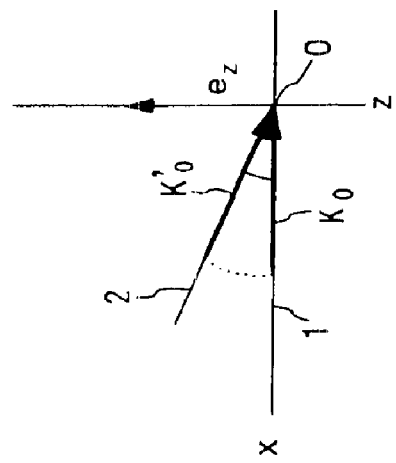
FIG. 3C is a left side view explaining the principle of the pole measuring method according to the present invention, as a follow-up view to FIG. 2.
Figure 4A:
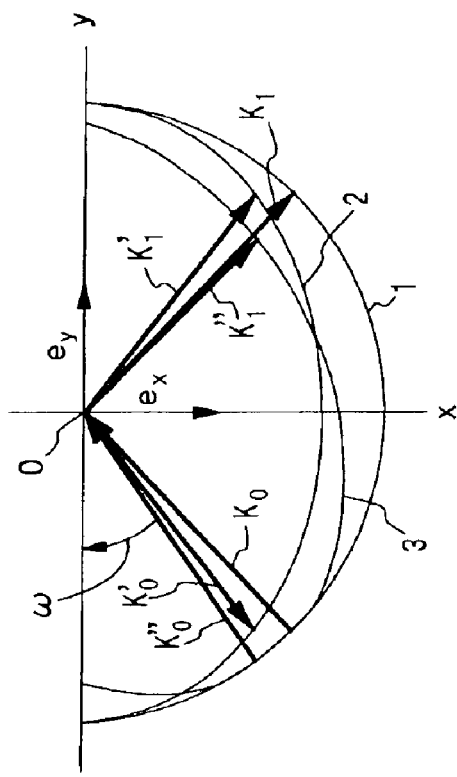
FIG. 4A is a plan view explaining the principle of the pole measuring method according to the present invention, as a follow-up view to FIG. 3A.
Figure 4B:
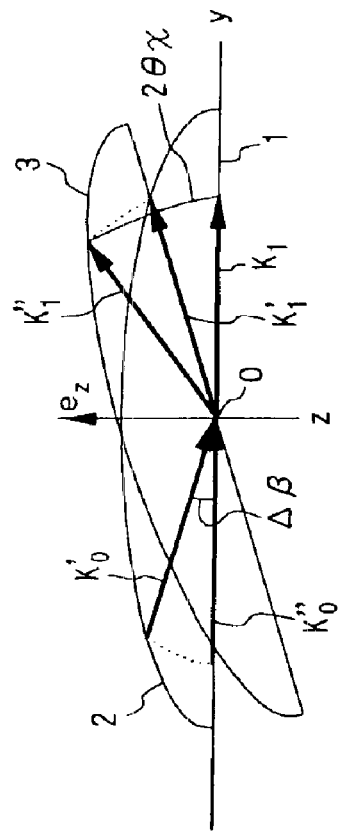
FIG. 4B is a front view explaining the principle of the pole measuring method according to the present invention, as a follow-up view to FIG. 3B.
Figure 4C:
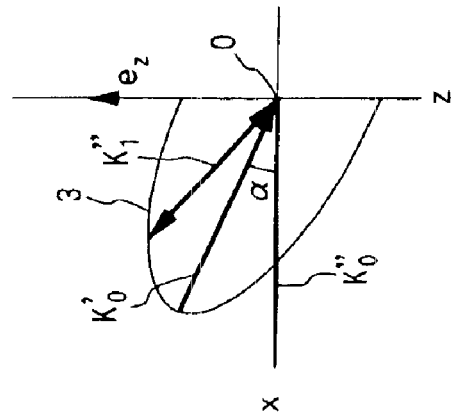
FIG. 4c is a left side view explaining the principle of the pole measuring method according to the present invention, as a follow-up view to FIG. 3C.

FIG. 2, FIGS. 3A to 3C, and FIGS. 4A to 4C are views explaining the principle of the pole measuring method according to the present invention, wherein FIGS. 2, 3A, and 4A are plan views, wherein FIGS. 3B and 4B are front views, and wherein FIGS. 3C and 4C are left side views.

With reference to these figures, the principle of the pole measuring method according to the present invention will be now described.

Consider x, y, and z orthogonal coordinate axes intersecting one another at an origin, in which the Φ axis in the in-plane diffractometer shown in FIG. 1 is defined as an x-axis, in which the Ω axis thereof is defined as a z-axis, and in which the axis corresponding to a tilting axis on the sample surface Sa is defined as z-axis.

As shown in FIG. 2, the wave number vectors of an incident X-ray, a diffracted X-ray, and a scattered X-ray, when the tilting angle α=90°, are denotes as $K_0$, $K_1$, and K, respectively, and thereby a diffraction plane 1, on which these vectors exist, is defined on the equator plane.

Next, as shown in FIGS. 3A to 3C, a diffraction plane 2, wherein the diffraction plane 1 is tilted about the y-axis by a tilting angle α, is defined, and the wave number vectors of an incident X-ray, a diffracted X-ray, and a scattered X-ray on the diffraction plane 2 are denotes as $K_0'$, $K_1'$, and $K'$, respectively.

Furthermore, the diffraction plane 2 is rotated about the x-axis by an angle of $\Delta\beta$ in the counterclockwise direction in FIG. 4B, and the wave number vector $K_0'$ of an incident X-ray on this diffraction plane 2, are placed on the diffraction plane 1. In this manner, the diffraction plane 2, which has been rotated by the angle of $\Delta\beta$ is defined as a diffraction plane 3, and the wave number vectors of an incident X-ray, a diffracted X-ray, and a scattered X-ray on the diffraction plane 3 are denotes as $K_0''$, $K_1''$, and $K''$, respectively.

In the pole measuring method according to the present invention, the incident angle ω of an incident X-ray $X_0$ with respect to the sample surface, and the angles of 2θ- and $2\theta_\chi$-revolutions of the X-ray detector 1 are set so as to satisfy the diffraction condition of the above-described diffraction plane 3 with respect to a preset tilting angle α of the sample S. Also, on the basis of the above-mentioned preset tilting angle α of the sample S, a correction angle $\Delta\beta$ with respect to the measuring angle of the sample in an in-plane rotational direction, is calculated. Then, a measuring angle φ of the sample in the in-plane rotational direction, obtained by adding the above-mentioned $\Delta\beta$ to a preset measuring angle β of the sample in the in-plane rotational direction, is set, and pole measuring of the sample is performed.

When rotation matrices about the coordinate axes x, y, and z are designated by Rx, Ry, and Rz, respectively, rotation matrices Rx(δ), Ry(δ), and Rz(δ) at a rotation angle δ are expressed by the following expressions.

$$Rx(\delta) \equiv \begin{pmatrix} 1 & 0 & 0 \\ 0 & \cos\delta & -\sin\delta \\ 0 & \sin\delta & \cos\delta \end{pmatrix} \quad (1)$$

$$Ry(\delta) \equiv \begin{pmatrix} \cos\delta & 0 & \sin\delta \\ 0 & 1 & 0 \\ -\sin\delta & 0 & \cos\delta \end{pmatrix} \quad (2)$$

$$Rz(\delta) \equiv \begin{pmatrix} \cos\delta & -\sin\delta & 0 \\ \sin\delta & \cos\delta & 0 \\ 0 & 0 & 1 \end{pmatrix} \quad (3)$$

Next, when unit vectors on the x, y, and z coordinate axis are denoted as $e_x$, $e_y$, and $e_z$, respectively, and a specified Bragg angle of a reflection is denoted as θb, the wave number vector $K_0$ of the incident X-ray, the wave number vector $K_1$ of the diffracted X-ray, and the wave number vector K of the scattered X-ray each of which exists on the above-described first diffraction plane 1, are expressed by the following expressions using the above-described equation (3).

$$K_1 = Rz(-2\theta b)K_0 \quad (4)$$

$$K = K_1 - K_0 \quad (5)$$

Therefore, the wave number vector $K_0'$ of the incident X-ray, the wave number vector $K_1'$ of the diffracted X-ray, and the wave number vector $K'$ of the scattered X-ray each of which exists on the above-described second diffraction plane 2, are expressed by the following expressions.

$$K_0' = Ry(-\alpha)K_0 \quad (6)$$

$$K_1' = Ry(-\alpha)K_1 \quad (7)$$

$$K' = K_1' - K_0' \quad (8)$$

Thereby, the correction angle $\Delta\beta$ with respect to the measuring angle of the sample surface Sa in the in-plane rotational direction can be obtained by the following expressions.

$$\Delta\beta = \cos^{-1}\frac{e_z \cdot (K_0 \times e_x)}{|e_z||K_0 \times e_x|} \quad (9)$$

$$K_0'' = Rx(\Delta\beta)K_0' \quad (10)$$

$$K_1'' = Rx(\Delta\beta)K_1' \quad (11)$$

Next, in the in-plane diffractometer, the X-ray incident angle ω, the pivoting angles 2θ and $2\theta_\chi$ of the X-ray detector, and the measuring angle φ of the sample surface Sa in the in-plane rotational direction, are obtained by the following expressions. Here, β in the equation (15) is a preset measuring angle of the sample in an in-plane rotational direction.

$$\omega = \cos^{-1}\frac{e_y \cdot (K_0'')}{|e_y||K_0''|} \quad (12)$$

$$2\theta = \omega + \cos^{-1}\frac{e_x \cdot (K_1' \times e_z)}{|e_x||K_1' \times e_z|} \quad (13)$$

$$2\theta_\chi = 90° - \cos^{-1}\frac{e_z \cdot (K_1'')}{|e_z||K_1''|} \quad (14)$$

$$\phi = \beta + \Delta\beta - 180° \quad (15)$$

Here, in the equation (15), φ is set to be an angle obtained by subtracting 180° from $\Delta\beta$. This is because the actual rotational direction of the tilting angle α is opposite to the rotational direction of the diffraction plane 2 shown in FIGS. 3A to 3C. A correction of direction is thus conducted by the equation (15).

In the pole measuring method according to the present invention, by using the above-described equations (13) and (14), set values of ω, 2θ, and $2\theta_\chi$ are calculated on the basis of the preset tilting angle α of the sample, and the in-plane diffractometer is set to these set values. Then, the measuring angle φ of the sample S in the in-plane rotational direction, which has been obtained from the equation (15), is set, and a pole is measured. Since the pole measuring method according to the present invention involves no tilting operation with respect to the sample, pole measuring by the reflection method can be performed over all measurement regions ranging from the region of high-tilting-angle α to the in-plane diffraction region.

Industrial Applicability

As described above, according to the present invention, it is possible to achieve pole measuring by the reflection method, over all measurement regions ranging from the region of high-tilting-angle α to the in-plane diffraction region, and to obtain highly accurate pole measuring data even with respect to thin samples or thick samples to be obtained.

What is claimed is:

1. A pole measuring method for measuring a pole of a sample, the method comprising the steps of:

setting an incident angle (ω) of an X-ray with respect to the surface of a sample to a predetermined position corresponding to the pole measuring position, when the sample is tilted by a preset tilting angle (α), by rotating the sample about a predetermined axis (Ω axis) passing through a predetermined origin (O), on the basis of the preset tilting angle (α) of the sample;

revolving an X-ray detector by an angle (2θ) about said predetermined axis (Ω axis) along a first plane perpendicular to said predetermined axis (Ω axis) and revolving the X-ray detector by an angle (2θ$_χ$) about the origin (O) along a second plane including said predetermined axis (Ω axis) and perpendicular to said first plane, on the basis of said preset tilting angle (α), whereby the X-ray detector is disposed at a predetermined position corresponding to a pole measuring position when the sample is tilted by said preset tilting angle (α);

calculating a correction angle (Δβ) with respect to a measuring angle (φ) of the sample in an in-plane rotational direction on the basis of said preset tilting angle (α), and setting the measuring angle (φ) of the sample in the in-plane rotational direction, said measuring angle (φ) being obtained by adding said correction angle (Δβ) to a preset measuring angle (β) of the sample in the in-plane rotational direction; and detecting X-rays diffracted from the surface of the sample using said X-ray detector.

2. A pole measuring method for measuring a pole of a sample, said method using an X-ray diffractometer operable for rotating a sample about a predetermined axis (Ω axis) passing through a predetermined origin (O), revolving an X-ray detector by an angle (2θ) about said predetermined axis (Ω axis) along a first plane perpendicular to said predetermined axis (Ω axis), revolving the X-ray detector by an angle (2θ$_χ$) about the origin (O) along a second plane including said predetermined axis (Ω axis) and perpendicular to said first plane, and in-plane rotating the sample about a predetermined axis (Φ axis) passing through said origin (O), said method comprising the steps of:

(a) setting an incident angle (ω) of an X-ray with respect to the surface of a sample to a predetermined position corresponding to a pole measuring position when the sample is tilted by a preset tilting angle (α) by rotating the sample about a predetermined axis (Ω axis) passing through a predetermined origin (O), on the basis of said preset tilting angle (α) of the sample;

(b) revolving the X-ray detector by an angle (2θ) about said predetermined axis (Ω axis) along a first plane perpendicular to said predetermined axis (Ω axis) and revolving the X-ray detector by an angle (2θ$_χ$) about the origin (O) along a second plane including said predetermined axis (Ω axis) and perpendicular to the plane perpendicular to said first axis, on the basis of said preset tilting angle (α), whereby the X-ray detector is disposed at a predetermined position corresponding to the pole measuring position when the sample is tilted by said preset tilting angle (α);

(c) calculating a correction angle (Δβ) with respect to measuring angle (φ) of the sample in an in-plane rotational direction on the basis of said preset tilting angle (α), and setting the measuring angle (φ) of the sample in the in-plane rotational direction, said measuring angle (φ) being obtained by adding said correction angle (Δβ) to a preset measuring angle (β) of the sample in the in-plane rotational direction; and (d) detecting X-rays diffracted from the surface of the sample using said X-ray detector, after said steps (a) to (c) have been completed.

3. A pole measuring method for measuring a pole of a sample according to claim 1 or 2, wherein, on the basis of the preset tilting angle (α) of the sample, said incident angle (ω) of an X-ray, pivoting angles (2θ and 2θ$_χ$) of the X-ray detector, and measuring angle (φ) of the sample in an in-plane rotational direction, are calculated by the following expressions, and are set, $$\omega = \cos^{-1} \frac{e_y \cdot (K_0'')}{|e_y||K_0''|}$$

$$2\theta = \omega + \cos^{-1} \frac{e_x \cdot (K_1' \times e_z)}{|e_x||K_1' \times e_z|}$$

$$2\theta\chi = 90° - \cos^{-1} \frac{e_z \cdot (K_1'')}{|e_z||K_1''|}$$

$$\phi = \beta + \Delta\beta - 180°$$

$$\Delta\beta = \cos^{-1} \frac{e_z \cdot (K_0 \times e_x)}{|e_z||K_0 \times e_x|}$$

wherein $e_x$, $e_y$, and $e_z$, respectively, are unit vectors on x, y, and z orthogonal coordinate axes intersecting one another at an origin, in which the in-plane rotational axis (Φ axis) of the sample is defined as an x-axis, in which said Ω axis is defined as a z-axis, and in which the axis corresponding to the tilting axis on the sample surface is defined as a y-axis, and wherein b is a preset measuring angle of the sample in an in-plane rotational direction, wherein, when rotation matrix about the x-axis is denoted as Rx, $K_0''=Rx(\Delta\beta)K_0'$ $K_1''=Rx(\Delta\beta)K_1'$ and wherein, when rotation matrices about the y-axis and z-axis are denoted as Ry and Rz, respectively, $K_0'=Ry(-\alpha)K_0$ $K_1'=Ry(-\alpha)K_1$ $K'=K_1'-K_0'$ $K_1=Rz(-2\theta_b)K_0$ where $\theta_b$ is a specified preset Bragg angle of reflection and $K_0$ is a wave number vector of an incident X-ray which is set with respect to this Bragg angle.

* * * * *

UNITED STATES PATENT AND TRADEMARK OFFICE
CERTIFICATE OF CORRECTION

| | | |
|---|---|---|
| PATENT NO. | : 6,937,694 B2 | Page 1 of 1 |
| APPLICATION NO. | : 10/129415 | |
| DATED | : August 30, 2005 | |
| INVENTOR(S) | : Ryouichi Yokoyama et al. | |

It is certified that error appears in the above-identified patent and that said Letters Patent is hereby corrected as shown below:

<u>Title page,</u>
Item [22], PCT Filed, delete "May 1, 2002" and substitute -- December 14, 2000 --;
Insert Items:
-- [86] PCT No.:     PCT/JP00/08876
   § 371 (c)(1),
   (2), (4) Date:    August 6, 2002
   [87] PCT Pub. No.:  WO0248696
        PCT Pub. Date: June 20, 2002 --.

Signed and Sealed this

Twenty-seventh Day of June, 2006

JON W. DUDAS
*Director of the United States Patent and Trademark Office*